US008012182B2

(12) United States Patent
Couedic et al.

(10) Patent No.: US 8,012,182 B2
(45) Date of Patent: Sep. 6, 2011

(54) SEMI-RIGID LINKING PIECE FOR STABILIZING THE SPINE

(75) Inventors: Régis Le Couedic, Bordeaux (FR); Denis Pasquet, Pessac (FR)

(73) Assignee: Zimmer Spine S.A.S., Bordeaux (FR)

( * ) Notice: Subject to any disclaimer, the term of this patent is extended or adjusted under 35 U.S.C. 154(b) by 110 days.

(21) Appl. No.: 11/726,820

(22) Filed: Mar. 22, 2007

(65) Prior Publication Data

US 2007/0288093 A1 Dec. 13, 2007

Related U.S. Application Data

(63) Continuation of application No. 10/333,284, filed as application No. PCT/FR01/02425 on Jul. 25, 2001, now abandoned.

(30) Foreign Application Priority Data

Jul. 25, 2000 (FR) ...................................... 00 09705

(51) Int. Cl.
*A61B 17/70* (2006.01)
(52) U.S. Cl. ........................................................ 606/264
(58) Field of Classification Search ................ 623/11.11, 623/16.11, 17.11–17.16; 606/246, 254–257, 606/259–261
See application file for complete search history.

(56) References Cited

U.S. PATENT DOCUMENTS

| | | |
|---|---|---|
| 2,515,366 A | 7/1950 | Zublin |
| 2,585,207 A | 2/1952 | Zublin |
| 2,649,092 A | 8/1953 | Wallace |
| 3,669,133 A | 6/1972 | Hyman |
| 4,328,839 A | 5/1982 | Lyons et al. |
| 4,648,388 A | 3/1987 | Steffee |
| 4,693,240 A | 9/1987 | Evans |
| 4,697,582 A | 10/1987 | William |
| 4,743,260 A | 5/1988 | Burton |
| 4,763,644 A | 8/1988 | Webb |
| 4,773,402 A | 9/1988 | Asher et al. |
| 4,805,602 A | 2/1989 | Puno et al. |
| 4,887,596 A | 12/1989 | Sherman |
| 4,892,552 A | 1/1990 | Ainsworth et al. |

(Continued)

FOREIGN PATENT DOCUMENTS

DE 4243951 7/1994

(Continued)

OTHER PUBLICATIONS

IPRP dated Sep. 27, 2007 for PCT/2006/008232.

(Continued)

*Primary Examiner* — Anu Ramana
(74) *Attorney, Agent, or Firm* — Spinkle IP Law Group

(57) ABSTRACT

The invention relates to a connecting member for maintaining the spacing between at least two anchor members screwed into vertebrae. The connecting member comprises: a flexible part (10) divided into two branches (12, 14), the ends of said branches being interconnected in pairs and defining a first median plane (Pm), and two rigid rod-forming parts (20, 22) each having a fixing first portion (20', 22') and a second portion (20", 22"), each of said second portions (20", 22") of said two rigid parts (20, 22) extending respective ends of said branches interconnected in pairs in opposite directions, so that said connecting member, whose fixing portions (20', 22') are fixed to respective anchor members, is able to bend elastically in a direction perpendicular to said median plane (Pm).

18 Claims, 2 Drawing Sheets

U.S. PATENT DOCUMENTS

Figure 1:
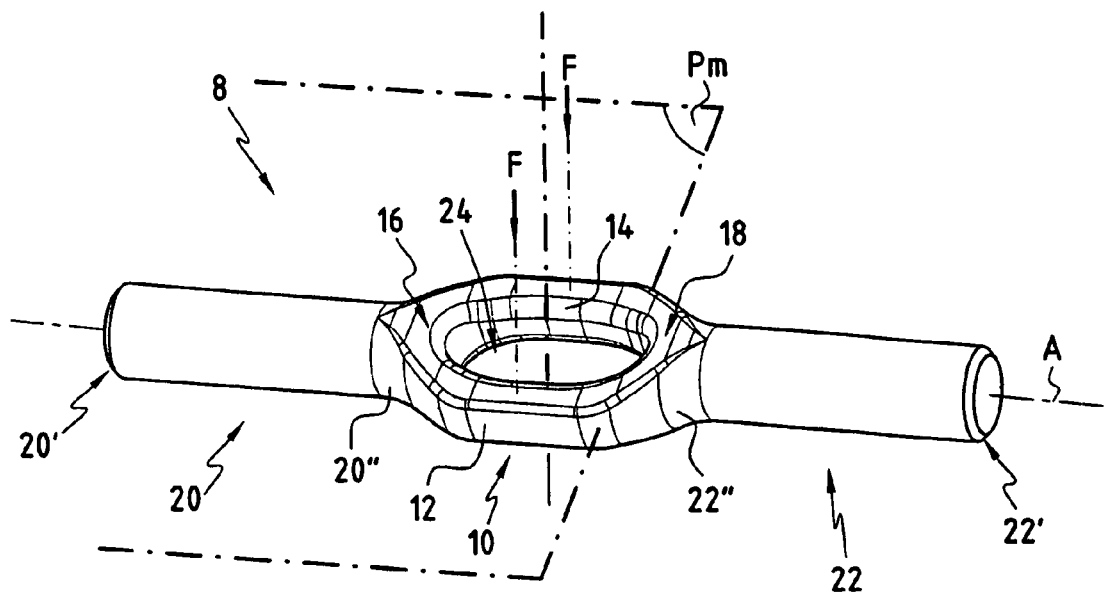

| | | |
|---|---|---|
| 4,917,700 A | 4/1990 | Aikins |
| 4,932,975 A | 6/1990 | Main et al. |
| 4,946,378 A | 8/1990 | Hirayama et al. |
| 4,950,269 A | 8/1990 | Gaines |
| 5,002,576 A | 3/1991 | Fuhrmann et al. |
| 5,011,497 A | 4/1991 | Persson et al. |
| 5,034,011 A | 7/1991 | Howland |
| 5,092,866 A | 3/1992 | Breard et al. |
| 5,102,412 A | 4/1992 | Rogozinski |
| 5,129,388 A | 7/1992 | Vignaud et al. |
| 5,154,718 A | 10/1992 | Cozad et al. |
| 5,176,680 A | 1/1993 | Vignaud et al. |
| 5,176,708 A | 1/1993 | Frey et al. |
| 5,181,917 A | 1/1993 | Rogozinski |
| 5,190,543 A | 3/1993 | Schlapfer |
| 5,217,450 A | 6/1993 | Pryor et al. |
| 5,282,863 A | 2/1994 | Burton |
| 5,334,203 A | 8/1994 | Wagner |
| 5,366,455 A | 11/1994 | Dove et al. |
| 5,368,594 A | 11/1994 | Martin et al. |
| 5,375,823 A | 12/1994 | Navas |
| 5,413,576 A | 5/1995 | Rivard |
| 5,413,602 A | 5/1995 | Metz-Stavenhagen |
| 5,415,661 A | 5/1995 | Holmes |
| 5,423,816 A | 6/1995 | Lin |
| 5,423,817 A | 6/1995 | Lin |
| 5,423,819 A | 6/1995 | Small |
| 5,426,816 A | 6/1995 | Chen |
| 5,456,722 A | 10/1995 | McLeod et al. |
| 5,480,401 A | 1/1996 | Navas |
| 5,486,174 A | 1/1996 | Fournet-Fayard et al. |
| 5,488,761 A | 2/1996 | Leone |
| 5,496,318 A | 3/1996 | Howland et al. |
| 5,508,093 A | 4/1996 | Mehdorn |
| 5,522,816 A | 6/1996 | Dinello et al. |
| 5,536,268 A | 7/1996 | Griss |
| 5,540,688 A | 7/1996 | Navas |
| 5,562,660 A | 10/1996 | Grob |
| 5,562,737 A | 10/1996 | Graf |
| 5,569,246 A | 10/1996 | Ojima et al. |
| 5,591,165 A | 1/1997 | Jackson |
| 5,591,235 A * | 1/1997 | Kuslich ..................... 606/261 |
| 5,601,554 A | 2/1997 | Howland et al. |
| 5,609,634 A | 3/1997 | Voydeville |
| 5,611,800 A | 3/1997 | Davis et al. |
| 5,616,142 A | 4/1997 | Yuan et al. |
| 5,645,599 A | 7/1997 | Samani |
| 5,658,286 A | 8/1997 | Sava |
| 5,672,175 A | 9/1997 | Martin |
| 5,676,665 A | 10/1997 | Bryan |
| 5,725,582 A | 3/1998 | Bevan et al. |
| 5,733,284 A | 3/1998 | Martin |
| 5,752,955 A | 5/1998 | Errico |
| 5,782,831 A | 7/1998 | Sherman et al. |
| 5,810,815 A | 9/1998 | Morales |
| 5,888,201 A | 3/1999 | Stinson et al. |
| RE36,221 E | 6/1999 | Beard et al. |
| 5,928,233 A | 7/1999 | Apfelbaum |
| 5,928,284 A | 7/1999 | Mehdizadeh |
| 5,951,555 A | 9/1999 | Rehak et al. |
| 5,961,516 A | 10/1999 | Graf |
| 5,968,091 A | 10/1999 | Pinchuk |
| 5,982,233 A | 11/1999 | Hellmark et al. |
| 5,984,923 A | 11/1999 | Breard |
| 6,053,922 A | 4/2000 | Krause et al. |
| 6,080,157 A | 6/2000 | Cathro et al. |
| 6,162,223 A | 12/2000 | Orsak et al. |
| 6,206,882 B1 | 3/2001 | Cohen |
| 6,241,730 B1 | 6/2001 | Alby |
| 6,248,106 B1 | 6/2001 | Ferree |
| 6,267,764 B1 | 7/2001 | Elberg |
| 6,270,910 B1 | 8/2001 | Jaeger et al. |
| 6,290,700 B1 | 9/2001 | Schmotzer |
| 6,293,949 B1 | 9/2001 | Justis et al. |
| 6,296,643 B1 | 10/2001 | Hopf et al. |
| 6,306,136 B1 | 10/2001 | Baccelli |
| 6,312,431 B1 | 11/2001 | Asfora |
| 6,337,142 B2 | 1/2002 | Harder et al. |
| 6,352,557 B1 | 3/2002 | Ferree |
| 6,402,751 B1 | 6/2002 | Hoeck et al. |
| 6,419,702 B1 | 7/2002 | Ferree |
| 6,440,169 B1 | 8/2002 | Elberg et al. |
| 6,447,518 B1 | 9/2002 | Krause et al. |
| 6,447,546 B1 | 9/2002 | Bramlet |
| 6,491,626 B1 | 12/2002 | Stone et al. |
| 6,500,178 B2 | 12/2002 | Zucherman et al. |
| 6,551,321 B1 | 4/2003 | Burkinshaw et al. |
| 6,554,831 B1 | 4/2003 | Rivard et al. |
| 6,582,468 B1 | 6/2003 | Gauchet |
| 6,585,738 B1 | 7/2003 | Mangione |
| 6,602,293 B1 | 8/2003 | Biermann et al. |
| 6,610,062 B2 | 8/2003 | Bailey et al. |
| 6,610,079 B1 | 8/2003 | Li et al. |
| 6,616,669 B2 | 9/2003 | Ogilvie et al. |
| 6,626,904 B1 | 9/2003 | Jammet et al. |
| 6,626,944 B1 | 9/2003 | Taylor |
| 6,648,885 B1 | 11/2003 | Friesem |
| 6,652,585 B2 | 11/2003 | Lange |
| 6,656,184 B1 | 12/2003 | White et al. |
| 6,679,883 B2 | 1/2004 | Hawkes et al. |
| 6,695,842 B2 | 2/2004 | Zucherman et al. |
| 6,706,044 B2 | 3/2004 | Kuslich et al. |
| 6,723,335 B1 | 4/2004 | Moehlenbruck et al. |
| 6,733,534 B2 | 5/2004 | Sherman |
| 6,749,614 B2 | 6/2004 | Teitelbaum et al. |
| 6,752,831 B2 | 6/2004 | Sybert et al. |
| 6,761,719 B2 | 7/2004 | Justis et al. |
| 6,761,720 B1 | 7/2004 | Senegas |
| 6,783,527 B2 | 8/2004 | Drewry et al. |
| 6,802,844 B2 | 10/2004 | Ferree |
| 6,852,128 B2 | 2/2005 | Lange |
| 6,875,212 B2 | 4/2005 | Shaolian et al. |
| 6,899,713 B2 | 5/2005 | Shaolian et al. |
| 6,899,716 B2 | 5/2005 | Cragg |
| 6,921,403 B2 | 7/2005 | Cragg et al. |
| 6,929,660 B1 | 8/2005 | Ainsworth et al. |
| 6,946,000 B2 | 9/2005 | Senegas et al. |
| 6,964,667 B2 | 11/2005 | Shaolian et al. |
| 6,966,910 B2 | 11/2005 | Ritland |
| 6,986,771 B2 | 1/2006 | Paul et al. |
| 6,987,011 B1 | 1/2006 | Reid et al. |
| 6,989,011 B2 | 1/2006 | Paul et al. |
| 6,991,632 B2 | 1/2006 | Ritland |
| 7,008,424 B2 | 3/2006 | Teitelbaum |
| 7,018,379 B2 | 3/2006 | Drewry et al. |
| 7,029,475 B2 | 4/2006 | Panjabi |
| 7,029,495 B2 | 4/2006 | Stinson |
| 7,125,410 B2 | 10/2006 | Freudiger |
| 7,137,985 B2 | 11/2006 | Jahng |
| 7,175,626 B2 | 2/2007 | Neff |
| 7,250,052 B2 | 7/2007 | Landry et al. |
| 7,259,052 B2 | 8/2007 | Murata et al. |
| 7,326,210 B2 | 2/2008 | Jahng et al. |
| 7,329,258 B2 | 2/2008 | Studer |
| 7,413,576 B2 | 8/2008 | Sybert et al. |
| 7,588,601 B2 | 9/2009 | Le Couedic et al. |
| 7,621,912 B2 | 11/2009 | Harms et al. |
| 7,651,515 B2 | 1/2010 | Mack et al. |
| 7,763,052 B2 | 7/2010 | Jahng |
| 7,842,072 B2 | 11/2010 | Dawson |
| 2002/0035366 A1 | 3/2002 | Walder et al. |
| 2002/0052603 A1 | 5/2002 | Nichols et al. |
| 2002/0082598 A1 | 6/2002 | Teitelbaum |
| 2002/0082698 A1 | 6/2002 | Parenteau et al. |
| 2002/0120272 A1 | 8/2002 | Yuan et al. |
| 2002/0138077 A1 | 9/2002 | Ferree |
| 2003/0045874 A1 | 3/2003 | Thomas |
| 2003/0069639 A1 | 4/2003 | Sander et al. |
| 2003/0083657 A1 | 5/2003 | Drewry et al. |
| 2003/0109880 A1 | 6/2003 | Shirado et al. |
| 2003/0144666 A1 | 7/2003 | Bagga |
| 2003/0153915 A1 | 8/2003 | Nekozuka et al. |
| 2003/0171749 A1 | 9/2003 | Le Couedic et al. |
| 2003/0191470 A1 | 10/2003 | Ritland |
| 2003/0195628 A1 | 10/2003 | Bao et al. |
| 2003/0220643 A1 | 11/2003 | Ferree |
| 2004/0002708 A1 | 1/2004 | Ritland |

| | | | | | | |
|---|---|---|---|---|---|---|
| 2004/0015166 A1 | 1/2004 | Gorek | | 2006/0058790 A1 | 3/2006 | Carl et al. |
| 2004/0049188 A1 | 3/2004 | Slivka | | 2006/0058792 A1 | 3/2006 | Hynes |
| 2004/0049189 A1 | 3/2004 | Le Couedic et al. | | 2006/0064090 A1 | 3/2006 | Park |
| 2004/0049190 A1 | 3/2004 | Biedermann et al. | | 2006/0064169 A1 | 3/2006 | Ferree |
| 2004/0073215 A1 | 4/2004 | Carli | | 2006/0084982 A1 | 4/2006 | Kim |
| 2004/0078082 A1 | 4/2004 | Lange | | 2006/0084984 A1 | 4/2006 | Kim |
| 2004/0082954 A1 | 4/2004 | Teitelbaum et al. | | 2006/0084987 A1 | 4/2006 | Kim |
| 2004/0097931 A1 | 5/2004 | Mitchell | | 2006/0084993 A1 | 4/2006 | Landry et al. |
| 2004/0106995 A1 | 6/2004 | Le Couedic et al. | | 2006/0095035 A1 | 5/2006 | Jones et al. |
| 2004/0138662 A1 | 7/2004 | Landry et al. | | 2006/0106380 A1 | 5/2006 | Colleran |
| 2004/0143265 A1 | 7/2004 | Landry et al. | | 2006/0106382 A1 | 5/2006 | Gournay et al. |
| 2004/0167625 A1 | 8/2004 | Beyar et al. | | 2006/0111715 A1 | 5/2006 | Jackson |
| 2004/0172022 A1 | 9/2004 | Landry et al. | | 2006/0122597 A1 | 6/2006 | Jones et al. |
| 2004/0215191 A1 | 10/2004 | Kitchen | | 2006/0129147 A1 | 6/2006 | Biedermann et al. |
| 2004/0225289 A1 | 11/2004 | Biedermann et al. | | 2006/0142758 A1 | 6/2006 | Petit |
| 2004/0236328 A1 | 11/2004 | Paul | | 2006/0142760 A1 | 6/2006 | McDonnell |
| 2004/0236329 A1 | 11/2004 | Panjabi | | 2006/0142761 A1 | 6/2006 | Landry et al. |
| 2004/0267260 A1 | 12/2004 | Mack | | 2006/0149228 A1 | 7/2006 | Schlapfer et al. |
| 2005/0010220 A1 | 1/2005 | Casutt | | 2006/0149229 A1 | 7/2006 | Kwak et al. |
| 2005/0010293 A1 | 1/2005 | Zucherman et al. | | 2006/0173454 A1 | 8/2006 | Spitler et al. |
| 2005/0010298 A1 | 1/2005 | Zucherman et al. | | 2006/0184417 A1 | 8/2006 | Biedermann et al. |
| 2005/0033295 A1 | 2/2005 | Wisnewski | | 2006/0189982 A1 | 8/2006 | Lange |
| 2005/0043733 A1 | 2/2005 | Eisermann et al. | | 2006/0189983 A1 | 8/2006 | Fallin et al. |
| 2005/0056979 A1 | 3/2005 | Studer et al. | | 2006/0189984 A1 | 8/2006 | Fallin et al. |
| 2005/0065416 A1 | 3/2005 | Subotics | | 2006/0195088 A1 | 8/2006 | Sacher et al. |
| 2005/0065514 A1 | 3/2005 | Studer | | 2006/0195093 A1 | 8/2006 | Jahng |
| 2005/0065515 A1 | 3/2005 | Jahng | | 2006/0200129 A1 | 9/2006 | Denti |
| 2005/0065516 A1 | 3/2005 | Jahng | | 2006/0212033 A1 | 9/2006 | Rothman et al. |
| 2005/0075634 A1 | 4/2005 | Zucherman et al. | | 2006/0229608 A1 | 10/2006 | Foster et al. |
| 2005/0085814 A1 | 4/2005 | Sherman et al. | | 2006/0229609 A1 | 10/2006 | Wang |
| 2005/0085815 A1 | 4/2005 | Harms | | 2006/0229612 A1 | 10/2006 | Rothman et al. |
| 2005/0085914 A1 | 4/2005 | Lange et al. | | 2006/0229615 A1 | 10/2006 | Abdou |
| 2005/0096652 A1 | 5/2005 | Burton | | 2006/0235386 A1 | 10/2006 | Anderson |
| 2005/0101953 A1 | 5/2005 | Simonson | | 2006/0235390 A1 | 10/2006 | Zhang et al. |
| 2005/0107789 A1 | 5/2005 | Sweeney | | 2006/0235391 A1 | 10/2006 | Sutterlin, III |
| 2005/0113927 A1 | 5/2005 | Malek | | 2006/0240533 A1 | 10/2006 | Sengupta et al. |
| 2005/0113928 A1 | 5/2005 | Cragg et al. | | 2006/0241601 A1 | 10/2006 | Trautwein |
| 2005/0113929 A1 | 5/2005 | Cragg | | 2006/0241640 A1 | 10/2006 | Briard et al. |
| 2005/0124991 A1 | 6/2005 | Jahng | | 2006/0247635 A1 | 11/2006 | Gordon et al. |
| 2005/0125063 A1 | 6/2005 | Matge et al. | | 2006/0247637 A1 | 11/2006 | Colleran et al. |
| 2005/0131407 A1 | 6/2005 | Sicvol et al. | | 2006/0247638 A1 | 11/2006 | Trieu et al. |
| 2005/0143737 A1 | 6/2005 | Pafford | | 2006/0264935 A1 | 11/2006 | White |
| 2005/0143823 A1 | 6/2005 | Boyd et al. | | 2006/0264937 A1 | 11/2006 | White |
| 2005/0149020 A1 | 7/2005 | Jahng | | 2006/0271046 A1 | 11/2006 | Kwak et al. |
| 2005/0149022 A1 | 7/2005 | Shaolian | | 2006/0276247 A1 | 12/2006 | Martinez |
| 2005/0149023 A1 | 7/2005 | Ritland | | 2006/0282080 A1 | 12/2006 | Albert et al. |
| 2005/0149191 A1 | 7/2005 | Cragg et al. | | 2007/0005062 A1 | 1/2007 | Lange et al. |
| 2005/0154390 A1 | 7/2005 | Biedermann | | 2007/0005063 A1 | 1/2007 | Bruneau et al. |
| 2005/0177156 A1 | 8/2005 | Timm et al. | | 2007/0016190 A1 | 1/2007 | Martinez et al. |
| 2005/0177157 A1 | 8/2005 | Jahng | | 2007/0016193 A1 | 1/2007 | Ritland |
| 2005/0177160 A1 | 8/2005 | Baynham et al. | | 2007/0016200 A1 | 1/2007 | Jackson |
| 2005/0182400 A1 | 8/2005 | White | | 2007/0016204 A1 | 1/2007 | Martinez |
| 2005/0182401 A1 | 8/2005 | Timm et al. | | 2007/0049936 A1 | 3/2007 | Colleran et al. |
| 2005/0182409 A1 | 8/2005 | Callahan et al. | | 2007/0049937 A1 | 3/2007 | Matthis et al. |
| 2005/0203511 A1 | 9/2005 | Wilson-MacDonald | | 2007/0055244 A1 | 3/2007 | Jackson |
| 2005/0203512 A1 | 9/2005 | Hawkins et al. | | 2007/0055247 A1 | 3/2007 | Jahng |
| 2005/0203513 A1 | 9/2005 | Jahng et al. | | 2007/0073289 A1 | 3/2007 | Kwak et al. |
| 2005/0203514 A1 | 9/2005 | Jahng et al. | | 2007/0083201 A1 | 4/2007 | Jones et al. |
| 2005/0203517 A1 | 9/2005 | Jahng | | 2007/0088359 A1 | 4/2007 | Woods et al. |
| 2005/0203518 A1 | 9/2005 | Biedermann | | 2007/0093813 A1 | 4/2007 | Callahan, II et al. |
| 2005/0203519 A1 | 9/2005 | Harms | | 2007/0093814 A1 | 4/2007 | Callahan, II et al. |
| 2005/0203624 A1 | 9/2005 | Serhan et al. | | 2007/0093904 A1 | 4/2007 | Biedermann et al. |
| 2005/0222569 A1 | 10/2005 | Panjabi | | 2007/0100341 A1 | 5/2007 | Reglos et al. |
| 2005/0245929 A1 | 11/2005 | Winslow et al. | | 2007/0118119 A1 | 5/2007 | Hestad |
| 2005/0245930 A1 | 11/2005 | Timm et al. | | 2007/0118120 A1 | 5/2007 | Stevenson et al. |
| 2005/0261686 A1 | 11/2005 | Paul | | 2007/0123866 A1 | 5/2007 | Gerbec et al. |
| 2005/0277920 A1 | 12/2005 | Slivka | | 2007/0129729 A1 | 6/2007 | Petit et al. |
| 2005/0277922 A1 | 12/2005 | Trieu | | 2007/0135815 A1 | 6/2007 | Gerbec et al. |
| 2005/0277934 A1 | 12/2005 | Vardiman | | 2007/0150064 A1 | 6/2007 | Ruberte et al. |
| 2005/0283243 A1 | 12/2005 | Zucherman et al. | | 2007/0161993 A1 | 7/2007 | Lowery et al. |
| 2005/0288371 A1 | 12/2005 | Ebert | | 2007/0179503 A1 | 8/2007 | Ferree |
| 2005/0288670 A1 | 12/2005 | Panjabi et al. | | 2007/0179606 A1 | 8/2007 | Huyghe et al. |
| 2005/0288672 A1 | 12/2005 | Ferree | | 2007/0190230 A1 | 8/2007 | Trieu et al. |
| 2006/0009767 A1 | 1/2006 | Kiester | | 2007/0191832 A1 | 8/2007 | Trieu |
| 2006/0009768 A1 | 1/2006 | Ritland | | 2007/0198014 A1 | 8/2007 | Graf et al. |
| 2006/0009845 A1 | 1/2006 | Chin | | 2007/0198088 A1 | 8/2007 | Biedermann et al. |
| 2006/0036240 A1 | 2/2006 | Colleran | | 2007/0213719 A1 | 9/2007 | Hudgins et al. |
| 2006/0036244 A1 | 2/2006 | Spitler et al. | | 2007/0213829 A1 | 9/2007 | Le Couedic et al. |
| 2006/0041259 A1 | 2/2006 | Paul | | 2007/0219556 A1 | 9/2007 | Altarac et al. |

| | | | | | |
|---|---|---|---|---|---|
| 2007/0225710 A1 | 9/2007 | Jahng et al. | EP | 1620023 | 2/2006 |
| 2007/0233075 A1 | 10/2007 | Dawson | EP | 1658815 | 5/2006 |
| 2007/0233078 A1 | 10/2007 | Justis et al. | EP | 1719468 | 11/2006 |
| 2007/0233087 A1 | 10/2007 | Schlapfer | EP | 1815812 | 8/2007 |
| 2007/0233090 A1 | 10/2007 | Naifeh et al. | FR | 2676911 | 4/1992 |
| 2007/0233095 A1 | 10/2007 | Schlaepfer | FR | 2682280 | 4/1993 |
| 2007/0239158 A1 | 10/2007 | Trieu et al. | FR | 2694182 | 2/1994 |
| 2007/0244482 A1 | 10/2007 | Aferzon | FR | 2697428 | 5/1994 |
| 2007/0270821 A1 | 11/2007 | Trieu et al. | FR | 2715057 | 7/1995 |
| 2007/0270860 A1 | 11/2007 | Jackson | FR | 2728158 | 6/1996 |
| 2007/0270959 A1 | 11/2007 | Dubousset | FR | 2730405 | 8/1996 |
| 2007/0276380 A1 | 11/2007 | Jahng et al. | FR | 2735351 | 12/1996 |
| 2007/0288009 A1 | 12/2007 | Brown et al. | FR | 2 755 844 | 5/1998 |
| 2007/0288012 A1 | 12/2007 | Colleran et al. | FR | 2774581 | 8/1999 |
| 2007/0288094 A1 | 12/2007 | Krishna et al. | FR | 2775583 | 9/1999 |
| 2007/0293862 A1 | 12/2007 | Jackson | FR | 2799949 | 4/2001 |
| 2008/0009863 A1 | 1/2008 | Bond et al. | FR | 2817461 | 6/2002 |
| 2008/0015693 A1 | 1/2008 | Le Couedic | FR | 2844180 | 3/2004 |
| 2008/0021459 A1 | 1/2008 | Lim | FR | 2845268 | 4/2004 |
| 2008/0021465 A1 | 1/2008 | Shadduck et al. | FR | 2845587 | 4/2004 |
| 2008/0033435 A1 | 2/2008 | Studer et al. | FR | 2867057 | 9/2005 |
| 2008/0033557 A1 | 2/2008 | Pasquet et al. | FR | 2870106 | 11/2005 |
| 2008/0039843 A1 | 2/2008 | Abdou | FR | 2870109 | 11/2005 |
| 2008/0039943 A1 | 2/2008 | Le Couedic et al. | FR | 2870719 | 12/2005 |
| 2008/0058812 A1 | 3/2008 | Zehnder | FR | 2890850 | 3/2007 |
| 2008/0065073 A1 | 3/2008 | Perriello et al. | GB | 269753 A | 2/1994 |
| 2008/0091213 A1 | 4/2008 | Jackson | GB | 2269753 A | 2/1994 |
| 2008/0140076 A1 | 6/2008 | Jackson | GB | 2320198 A | 6/1998 |
| 2008/0140133 A1 | 6/2008 | Allard et al. | GB | 2382304 A | 5/2003 |
| 2008/0147122 A1 | 6/2008 | Jackson | JP | 2005305156 A | 11/2005 |
| 2008/0154307 A1 | 6/2008 | Colleran et al. | NL | 7610576 | 3/1978 |
| 2008/0161854 A1 | 7/2008 | Bae et al. | WO | WO9013265 | 11/1990 |
| 2008/0161857 A1 | 7/2008 | Hestad et al. | WO | WO9426192 | 11/1994 |
| 2008/0177316 A1 | 7/2008 | Bergeron et al. | WO | WO9505783 | 3/1995 |
| 2008/0177317 A1 | 7/2008 | Jackson | WO | WO9519149 | 7/1995 |
| 2008/0183213 A1 | 7/2008 | Veldman et al. | WO | WO9615729 | 5/1996 |
| 2008/0183216 A1 | 7/2008 | Jackson | WO | WO9641582 | 12/1996 |
| 2008/0195153 A1 | 8/2008 | Thompson | WO | WO9709940 | 3/1997 |
| 2008/0208256 A1 | 8/2008 | Thramann | WO | WO9732533 | 9/1997 |
| 2008/0234737 A1 | 9/2008 | Boschert | WO | WO 98/22033 * | 5/1998 |
| 2008/0234744 A1 | 9/2008 | Zylber et al. | WO | WO9905980 | 2/1999 |
| 2008/0262552 A1 | 10/2008 | Kim | WO | 99/40866 | 8/1999 |
| 2008/0294198 A1 | 11/2008 | Jackson | WO | WO0139678 | 6/2001 |
| 2008/0319486 A1 | 12/2008 | Hestad | WO | WO0145576 A1 | 6/2001 |
| 2009/0012562 A1 | 1/2009 | Hestad et al. | WO | WO0149192 | 7/2001 |
| 2009/0036924 A1 | 2/2009 | Egli et al. | WO | WO0164144 | 9/2001 |
| 2009/0270921 A1 | 10/2009 | Krause | WO | WO0207621 | 1/2002 |
| 2009/0326585 A1 | 12/2009 | Baccelli et al. | WO | WO0207622 | 1/2002 |
| | | | WO | WO0207622 A1 | 1/2002 |
| FOREIGN PATENT DOCUMENTS | | | WO | WO0217803 | 3/2002 |
| DE | 4239716 | 8/1994 | WO | WO0243603 | 6/2002 |
| EP | 0381588 | 8/1990 | WO | WO02067792 | 9/2002 |
| EP | 0478470 | 4/1992 | WO | WO02071960 | 9/2002 |
| EP | 0516567 | 12/1992 | WO | WO02102259 | 12/2002 |
| EP | 0538183 | 4/1993 | WO | WO03007828 | 1/2003 |
| EP | 0576379 | 12/1993 | WO | WO03015645 | 2/2003 |
| EP | 0611554 | 8/1994 | WO | WO03015646 | 2/2003 |
| EP | 0612507 | 8/1994 | WO | WO03047441 | 6/2003 |
| EP | 0649293 | 4/1995 | WO | WO03047442 | 6/2003 |
| EP | 0 667 127 | 8/1995 | WO | WO03077806 | 9/2003 |
| EP | 0669109 | 8/1995 | WO | WO03094699 | 11/2003 |
| EP | 0677277 | 10/1995 | WO | WO2004017817 | 3/2004 |
| EP | 0768843 | 4/1997 | WO | WO2004024011 | 3/2004 |
| EP | 1054638 | 11/2000 | WO | WO2004034916 | 4/2004 |
| EP | 1239785 | 9/2002 | WO | WO2004039283 | 5/2004 |
| EP | 1281361 | 2/2003 | WO | WO2004084743 | 10/2004 |
| EP | 1299042 | 4/2003 | WO | WO2004089244 | 10/2004 |
| EP | 1303224 | 4/2003 | WO | WO2004091413 | 10/2004 |
| EP | 1303225 | 4/2003 | WO | WO2004098423 | 11/2004 |
| EP | 1364622 | 11/2003 | WO | WO2004098452 | 11/2004 |
| EP | 1388323 | 2/2004 | WO | WO2005009300 | 2/2005 |
| EP | 1399078 | 3/2004 | WO | WO2005020860 | 3/2005 |
| EP | 1138268 | 10/2004 | WO | WO2005030066 | 4/2005 |
| EP | 1488751 | 12/2004 | WO | WO2005030067 | 4/2005 |
| EP | 1523949 | 4/2005 | WO | WO2005030068 | 4/2005 |
| EP | 1570795 | 9/2005 | WO | WO2005037110 | 4/2005 |
| EP | 1574173 | 9/2005 | WO | WO2005037150 | 4/2005 |
| EP | 1579816 | 9/2005 | WO | WO2005004413 | 5/2005 |
| EP | 1586276 | 10/2005 | WO | WO2005041795 | 5/2005 |

| | | |
|---|---|---|
| WO | WO2005065374 | 7/2005 |
| WO | WO2005065375 | 7/2005 |
| WO | WO2005087121 | 9/2005 |
| WO | WO2005118015 | 12/2005 |
| WO | WO2005120277 | 12/2005 |
| WO | WO2005120369 | 12/2005 |
| WO | WO2005122924 | 12/2005 |
| WO | WO2005122925 | 12/2005 |
| WO | WO2006002333 | 1/2006 |
| WO | WO2006002359 | 1/2006 |
| WO | WO2006017641 | 2/2006 |
| WO | WO2006020530 | 2/2006 |
| WO | WO2006066063 | 6/2006 |
| WO | WO2006066685 | 6/2006 |
| WO | WO2007044795 | 4/2007 |
| WO | WO2007087476 | 8/2007 |
| WO | WO 2007104024 | 9/2007 |
| WO | WO2008006098 | 1/2008 |
| WO | WO2008013892 | 1/2008 |
| WO | WO2008021319 | 2/2008 |
| WO | WO2008034130 | 3/2008 |

OTHER PUBLICATIONS

Written Opinion for PCT/US2009/038977 mailed Feb. 24, 2010, 7 pages.
Examination Report for Australian App. No. 2005249740 dated Mar. 4, 2010, 4 pages.
International Preliminary Report on Patentability issued in PCT/FR2005/001280 mailed Nov. 29, 2006, 13 pgs, and English translation, 7 pgs.
Written Opinion issued in PCT/FR2005/001280 mailed Nov. 7, 2005, 20 pgs.
International Preliminary Report on Patentability issued in PCT/FR2001/02426 mailed Oct. 22, 2002, Spine Next, 10 pages.
International Search Report issued in PCT/FR2001/02426, mailed Oct. 30, 2001, Spine Next, 6 pages.
International Search Report issued in PCT/FR2005/001280, mailed Nov. 7, 2005, Abbott Spine, 5 pages.
Office Action issued in U.S. Appl. No. 10/333,881, mailed May 1, 2006, 6 pages.
Office Action issued in U.S. Appl. No. 10/333,881, mailed Aug. 3, 2007, 6 pages.
Office Action issued in U.S. Appl. No. 10/333,881, mailed Sep. 6, 2005, 8 pages.
Office Action issued in U.S. Appl. No. 10/333,881, mailed Oct. 13, 2006, 6 pages.
Office Action issued in U.S. Appl. No. 10/333,881, mailed Oct. 27, 2008, 8 pages.
Office Action issued in U.S. Appl. No. 10/333,881, mailed Dec. 11, 2007, 6 pages.
Office Action issued in U.S. Appl. No. 10/333,881, mailed Dec. 16, 2004, 9 pages.
Office Action issued in U.S. Appl. No. 10/333,881, mailed Mar. 23, 2009, 7 pages.
Office Action issued in U.S. Appl. No. 10/333,881, mailed Jun. 27, 2008, 7 pages.
International Search Report and Written Opinion issued in PCT/US2006/008232, mailed Jul. 5, 2006, 13 pages.
Office Action issued in U.S. Appl. No. 11/564,930, mailed Apr. 22, 2009, 7 pages.
Office Action issued in U.S. Appl. No. 11/597,120, mailed Feb. 23, 2009, 9 pages.
Office Action issued in U.S. Appl. No. 11/597,120, mailed Sep. 30, 2008, 7 pages.
Patent Abstracts of Japan & JP 10 277070 "Artificial Intervertebral Joint," Oct. 20, 1998.
French Preliminary Search Report dated Jan. 12, 2005 in Patent Application No. FR0405611.
Bannon et al. "Titanium Alloys for Biomaterial Application: An Overview," Titanium Alloys in Surgical Implants, ASTM STP 796, Luckey et al., Eds., American Society for Testing and Materials, 1983. pp. 7-15.
Office Action issued in U.S. Appl. No. 11/082,297, mailed Apr. 24, 2009, 11 pages.
Office Action issued in U.S. Appl. No. 11/082,297, mailed Oct. 20, 2008, 18 pages.
Office Action issued in U.S. Appl. No. 11/082,297, mailed Mar. 20, 2008, 15 pages.
Office Action issued in U.S. Appl. No. 11/597,120, mailed Jun. 10, 2009, 11 pages.
Office Action issued in U.S. Appl. No. 10/333,284 mailed Dec. 14, 2004, 7 pages.
Office Action issued in U.S. Appl. No. 10/333,284 mailed Aug. 23, 2005, 8 pages.
Office Action issued in U.S. Appl. No. 10/333,284 mailed Mar. 24, 2006, 8 pages.
International Search Report issued for PCT Application No. PCT/US2009/0038977, mailed Jul. 22, 2009, 8 pages.
Written Opinion issued for PCT Application No. PCT/US2009/0038977, mailed Jul. 22, 2009, 4 pages.
International Search Report and Written Opinion for PCT/US2008/066896 mailed Nov. 25, 2009, 13 pages.
International Search Report and Written Opinion for PCT/US2009/060362 mailed Jan. 4, 2010, 10 pages.
Office Action issued in U.S. Appl. No. 11/868,183 mailed Jan. 12, 2010, 9 pages.
International Preliminary Report on Patentability issued in FR0009705 mailed Mar. 12, 2001, 1 page.
International Search Report for PCT/FR2001/02425, mailed Oct. 22, 2001, 2 pages.
Office Action issued in U.S. Appl. No. 11/597,120 mailed Jan. 5, 2010, 11 pages.
Examination Report issued for European Patent Application No. 08 771 000.0, mailed Apr. 29, 2010, 5 pgs.
International Preliminary Report on Patentability issued for PCT Application No. PCT/US2009/038977, completed and mailed on May 27, 2010, 7 pgs.
Office Action issued for U.S. Appl. No. 11/868,183, mailed Jun. 4, 2010, 14 pgs.
Office Action issued for U.S. Appl. No. 11/867,838, mailed Jul. 6, 2010, 14 pgs.
Office Action issued for U.S. Appl. No. 11/867,838, mailed Dec. 7, 2010, 13 pages.
Office Action issued for U.S. Appl. No. 12/059,634, mailed Feb. 15, 2011, 15 pages.
Final Office Action for U.S. Appl. No. 12/059,634 mailed Jun. 22, 2011, 15 pgs.
International Preliminary Report on Patentability for PCT Application No. PCT/US2009/060362, mailed on Feb. 17, 2011, 11 pgs.
Office Action for U.S. Appl. No. 12/340,366, mailed on Feb. 28, 2011, 9 pgs.
Office Action issued for U.S. Appl. No. 12/264,752, mailed on Mar. 9, 2011, 18 pgs.
Final Office Action issued for U.S. Appl. No. 11/867,838, mailed May 25, 2011, 17 pgs.
Office Action for U.S. Appl. No. 11/763,969, mailed on Jun. 10, 2011, 10 pgs.

* cited by examiner

SEMI-RIGID LINKING PIECE FOR STABILIZING THE SPINE

This application is a continuation of U.S. application Ser. No. 10/333,284 filed on Jan. 15, 2003, which is a National Stage of PCT/FR01/02425 filed on Jul. 25, 2001 which is the WIPO equivalent of French application 00/09705 filed on Jul. 25, 2000 which applications are incorporated herein by reference.

The present invention relates to a connecting member for maintaining the spacing between at least two anchor members which are interconnected by said connecting member.

Fields of application of the invention include stabilization and arthrodesis of segments of the vertebral column in degenerative pathologies of the spine.

Systems for stabilizing the vertebral column which brace at least two consecutive vertebrae by means of anchor members fixed into said vertebrae and connected by rigid connecting rods are well known in the art. Systems of this kind are generally coupled systems such that two consecutive vertebrae are interconnected by two substantially parallel rods fixed one on each side of the spinous processes. The anchor members are screwed into the posterior portion of the vertebrae and pass through the pedicles and a substantial portion of the vertebral bodies and therefore provide a fixed and durable connection.

The above stabilizing systems are routinely used to consolidate several consecutive vertebrae. Thus the vertebrae are interconnected by rigid rods over a substantial length of the vertebral column. Such assemblies hold the vertebrae correctly relative to each other; however, they considerably stiffen the spine in terms of bending. It has been shown that a more flexible stabilizing system, which confers greater relative mobility on the vertebrae, is beneficial in some pathologies.

Naturally enough, to increase the amplitude in bending of the stabilizing system, it has been proposed to reduce the section of the connecting rods between the anchor members to increase the amount by which said connecting rods deform for the same stress. This increases the mobility of the vertebrae relative to each other and also increases the amplitude of forward/rearward bending of the vertebral column for the same force. However, the vertebral column is not so well stabilized, in particular with regard to lateral stabilization of the vertebrae relative to each other. Also, stresses are higher in connecting rods of smaller section and the connecting rods may deteriorate prematurely.

A first object of the present invention is to provide a connecting member for maintaining the spacing between existing anchor members and which can bend more than the rods used at present without increasing the internal stresses in said connecting rods.

To achieve the above object, a connecting member in accordance with the invention for maintaining the spacing between at least two anchor members screwed into vertebrae comprises: a flexible part divided into two spaced continuous branches that are substantially symmetrical about a longitudinal axis of said member, the ends of said branches being interconnected in pairs and defining a first median plane, and two rigid rod-forming parts each having a fixing first portion and a second portion, each of said second portions of said two rigid parts respectively extending said ends of said branches interconnected in pairs in opposite directions, the cross-section of each of said branches being less than the cross-section of said rigid parts so that said connecting member, said fixing portions of which are fixed to respective anchor members, is able to bend elastically about an axis that is perpendicular to the longitudinal axis, said perpendicular axis being contained in said median plane of the connecting member on relative movement of the vertebrae, whereby the vertebrae, which are held spaced relative to each other, are movable relative to each other.

Thus one characteristic feature of the connecting member is its shape, which is such that the stresses exerted on its rigid parts by bending of the spine cause the two branches to bend in a direction perpendicular to the median plane that they define. This is because the connecting member can bend only in a direction perpendicular to the median plane that the two branches define because the two branches are joined at each end by the rigid parts and bending about another axis would longitudinally elongate one of the branches and longitudinally compress the other one; given the stresses, this would cause little deformation. In this way, the connecting member has a specific bending direction perpendicular to its main axis and is disposed so that the median plane defined by the two branches is substantially perpendicular to the plane in which the spine is able to bend. As explained in more detail below, the section of each of the continuous branches, which is substantially constant, is smaller than the section of the rigid parts, which increases the amplitude by which the member bends for the same force. Also, the bending stresses, representative of the internal forces in the two branches, are lower than the stresses to which a single branch would be subjected when bent by the same amount by the same force. This reduces fatigue of the connecting member of the invention.

The connecting member is advantageously adapted to interconnect n anchor members and comprises n rigid parts between which there are disposed n−1 flexible parts along the longitudinal axis of said member, each rigid part situated between two flexible parts having a first or fixing portion and two second portions, each of said second portions being situated at a respective end of said first or fixing portion, said second portions extending respective ends of the branches of said two flexible parts so that the median planes of all the flexible parts are substantially the same, and the rigid parts situated at the ends of said member advantageously have respective single second portions extending the ends of the branches of the flexible parts.

Thus, by virtue of this feature, the connecting member maintains the spacing between all the anchor members that it interconnects, each of which is fixed to a vertebra, to align them. Each rigid part is fixed to an anchor member and between the anchor members of each pair there is a flexible part extended by said rigid parts. In this way, a single connecting member stabilizes a plurality of vertebrae, which reduces the time needed to assemble the stabilizing system as a whole, and consequently the operating time. Also, this feature of the connecting member stabilizes a plurality of consecutive vertebrae by connecting them together, while at the same time allowing them great relative flexibility.

In a particular embodiment of said connecting member, the sum of the surface areas of the sections of said two branches is less than the surface area of the section of said rigid rod-forming parts. Thus the rigid rod-forming parts are more rigid than the two branches which bend more readily, said rigid parts being securely connected to said anchor members.

In another particular embodiment of the invention said branches have portions parallel to each other and to the longitudinal axis of said member and the distance between said branches is at least equal to the length of said portions. This configuration provides a connecting member which can bend much more in a direction perpendicular to the median plane defined by the branches than in any other direction; thus, allowing for the forces exerted on it, the connecting member has a single bending direction.

In a further particular embodiment of the invention, the distance between the ends of said branches connected in pairs lies in the range 1.5 times to 2.5 times the distance between said branches. This allows increased bending compared to the connecting rods routinely used, while at the same time obtaining a single bending direction perpendicular to the median plane defined by the two branches.

Also, the section of said rigid rod-forming parts is advantageously circular, which facilitates manufacture of the member, which is preferably made of titanium alloy. Also, if prior art circular section connecting rods are to be replaced by connecting members conforming to the invention without making it necessary to replace the anchor members, it is necessary for said rigid parts to have sections identical to the sections of prior art connecting rods.

Titanium alloys have mechanical and corrosion resistant properties compatible with the technical specifications required of the connecting member.

The present invention also provides a vertebral stabilization system for fastening together at least two vertebrae each having a median plane substantially perpendicular to the axis of the spine of which they are part and a posterior wall defining a posterior median plane of said spine, said system comprising at least two anchor members each adapted to be fixed into the posterior wall of a vertebra so that a line which intersects said two anchor members is substantially parallel to said axis of the spine, which system further comprises a connecting member of the invention whose two rigid parts are adapted to interconnect said two anchor members so that said median plane defined by said two branches is substantially parallel to said posterior median plane of said spine, whereby said vertebrae, which are interconnected in their posterior portions, are relatively movable along said axis of said spine.

Figure 2:
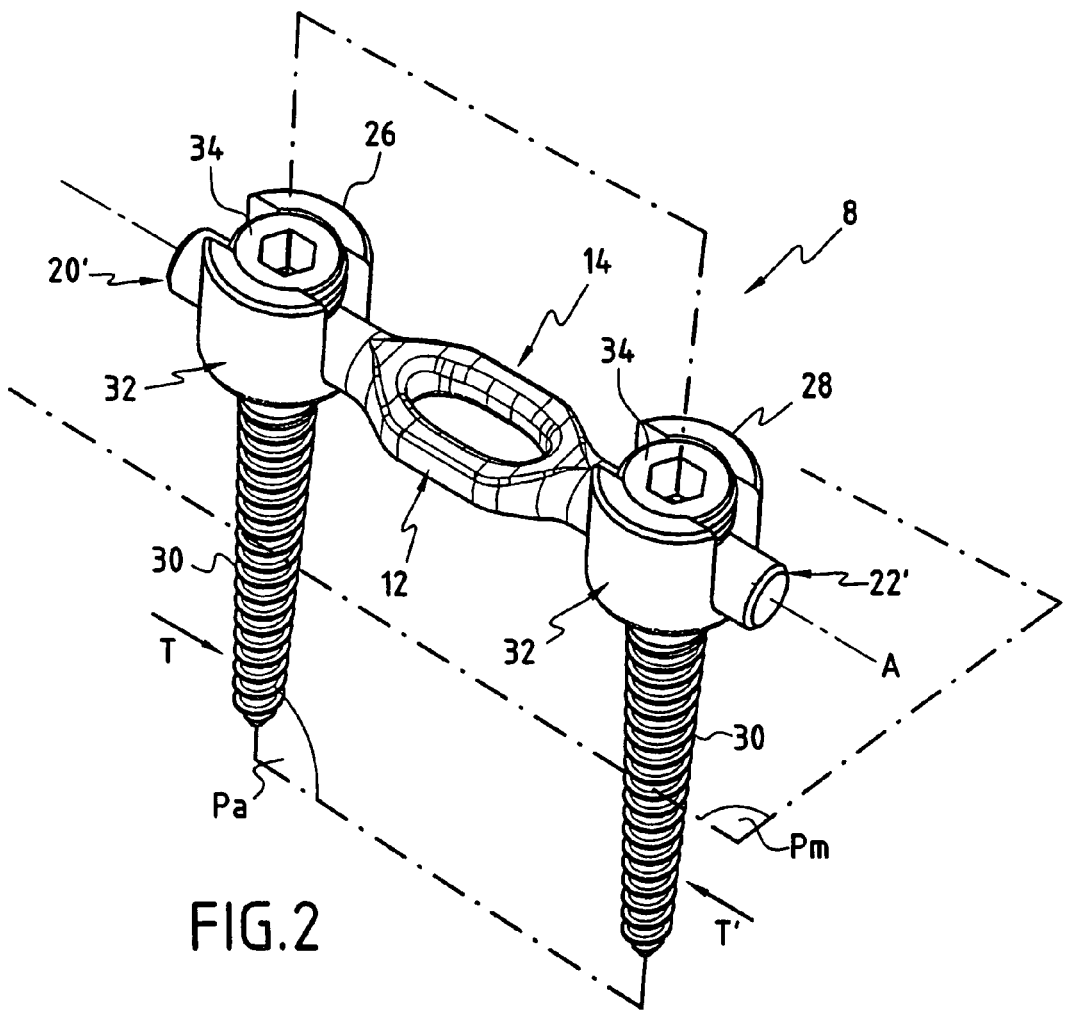
Figure 3:
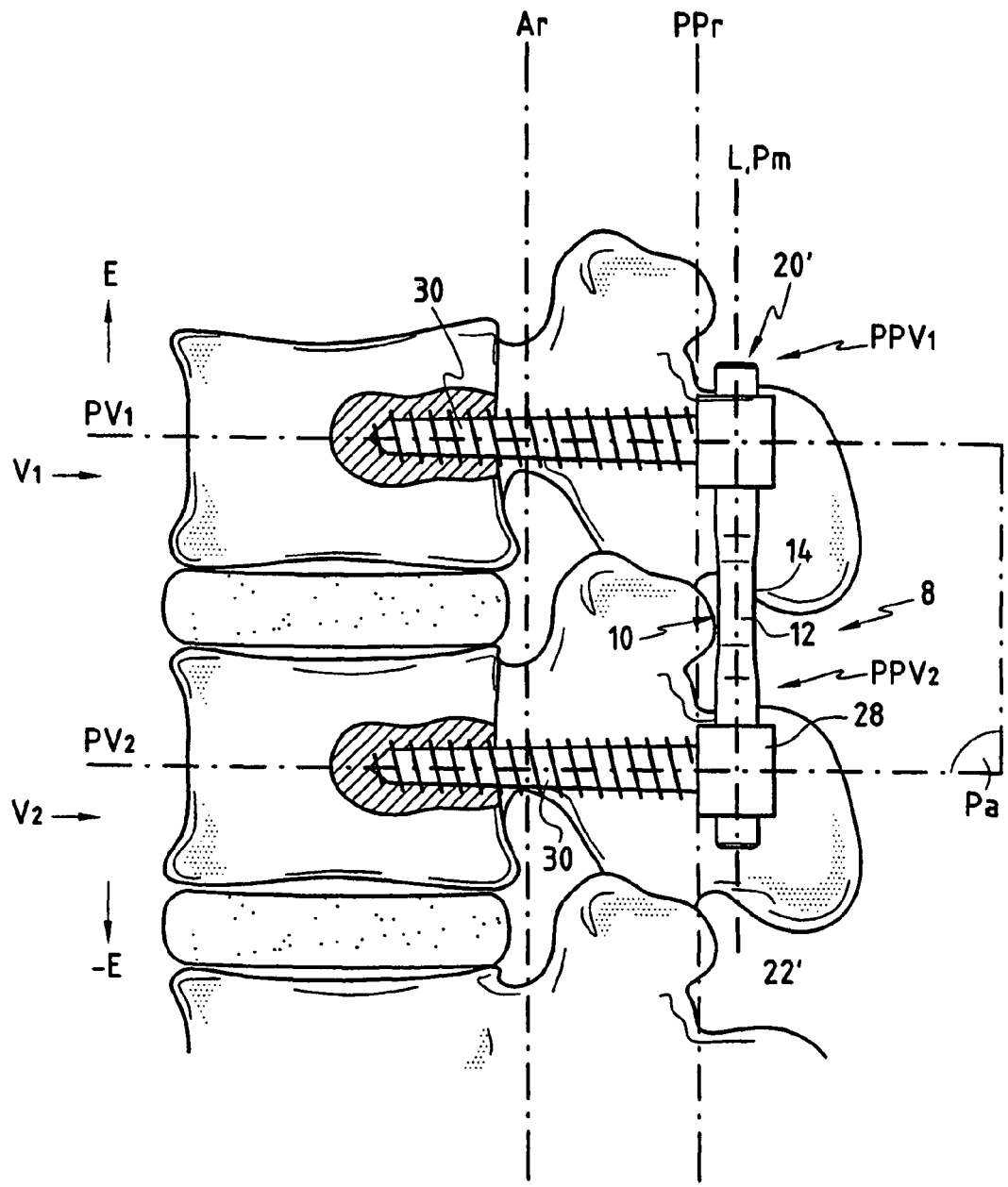

Other features and advantages of the invention will emerge on reading the following description of particular embodiments of the invention, which is given by way of non-limiting example and with reference to the accompanying drawings, in which:

FIG. 1 is a diagrammatic perspective view of a connecting member of the invention, FIG. 2 is a diagrammatic perspective view showing anchor members connected by the connecting member, and FIG. 3 is a diagrammatic side elevation view of a vertebral column showing two consecutive vertebrae into which there are screwed anchor members interconnected by a connecting member of the invention.

The various portions of a connecting member of the invention are described initially with reference to FIG. 1.

The connecting member 8 comprises a flexible part 10 having two parallel branches 12 and 14 interconnected at their ends at two points 16 and 18. Two rigid rod-forming parts 20 and 22 have respective fixing first portions 20',22' and second portions 20'',22'' extending the joined together ends of the two branches 12 and 14 from the two points 16 and 18 in opposite directions along a longitudinal axis A. The two parallel branches 12 and 14 joined at their ends therefore surround a void 24. They are also parallel to the axis A and symmetrical about that axis. The sum of the sections of the two branches 12 and 14 is preferably less than the section of the rigid parts which have substantially the same circular section, with the result that the diameter of the cross-section of a branch is less than 70% of the diameter of the rigid parts. For example, the diameter of the cross-section of a branch lies in the range 50% to 70% of the diameter of the rigid parts.

Also, the two branches 12 and 14 define a median plane Pm intersecting the two rigid parts 20 and 22 axially.

Thus the connecting member having the first fixing portions 20' and 22' of its rigid parts 20 and 22 in fixed bearing engagement, is itself able to bend elastically in a direction Dp perpendicular to the median plane Pm when a force F is exerted on each of the branches 12 and 14. This is because, given the section of the branches 12 and 14 relative to the section of the rigid parts 20 and 22, the radius of curvature of the connecting member when it bends is at a minimum at the center of the flexible part 10.

The sum of the forces F exerted on the branches in a direction perpendicular to the median plane Pm causing the connecting member to bend without breaking would not cause the connecting member to bend in a direction perpendicular to the axis A of the member and contained in the median plane Pm because, in this case, one of the branches would be in tension and the other in compression, which would prevent bending. A preferential bending direction is therefore obtained, which is advantageous in the context of the intended application, as explained in more detail below.

To obtain a preferential bending direction and an optimum bending amplitude, given the dimensions of the connecting portion, the two branches 12 and 14 are separated by a distance that is not less than the length of their parallel portions. Obviously, the closer together the branches 12,14, the greater the potential for bending about an axis not strictly perpendicular to the median plane Pm, and the force necessary to obtain said bending increases as the total length of the branches 12 and 14 decreases. However, the spacing between the two branches 12 and 14 is limited by the space available for inserting said member, both transversely and along the longitudinal axis, and consequently the distance between the ends of said branches connected in pairs is in the range 1.5 times to 2.5 times the distance between said branches.

To compare the stress to which a connecting member of the invention is subjected with the stress to which a simple prior art connecting rod is subjected, a rod of diameter 1 was made whose bending amplitude was to be increased by 50%. To achieve this, the diameter of the simple connecting rod had to be reduced by 10%, the consequence of which was a 35% increase in the stress in it. In contrast, to obtain the same amplitude of bending, the diameter of the branches of the connecting member of the invention had to represent 75% of the original diameter of the rod of diameter 1, although the stress in the branches was increased by only 13%.

The above measurements showed that, for the same bending, the connecting member of the invention was subjected to lower stresses than a conventional connecting rod, thereby reducing metal fatigue, so that its service life should be longer than prior art rods. Also, the lower the stresses in the connecting member, the better it retains its elastic properties.

Deformation of the connecting member on relative movement of the anchor members 26 and 28 is described below with reference to FIG. 2.

FIG. 2 shows the two rigid parts 20 and 22 of the connecting member interconnecting two anchor members 26 and 28. The two anchor members 26 and 28 are parallel to each other in a common axial plane Pa. The connecting member is fixed to the anchor members 26 and 28 so that the median plane Pm defined by the branches 12 and 14 is substantially perpendicular to the common axial plane Pa.

Each anchor member 26, 28 has a threaded shank 30 with a U-shaped head 32 at the top whose inside wall is threaded so that a screw-forming member 34 can be screwed into it. Thus the first or fixing portions 20' and 22' of the rigid parts 20 and 22 are accommodated in the heads 32 of the respective anchor members 26 and 28 and are locked to them by tightening the screw-forming members 34.

In this way, when the threaded shanks 30 of the anchor members tend to move towards each other due to the effect of opposite forces T and −T in the plane Pa and substantially parallel to the axis A, the anchor members 26 and 28 deform the connecting member to an arcuate shape in the plane Pa. The stress induces bending of the branches 12 and 14 of the connecting member in a direction perpendicular to the median plane Pm. When the stress is removed, the connecting member reverts to its original rectilinear shape and the threaded shanks of the anchor members 30 return to their former relative position.

The mechanism of elastic bending of the connecting member and the anchor members described above is the same if the threaded shanks 30 of the anchor members 26 and 28 move away from each other, the connecting member forming a reversed arcuate shape.

The use of the connection member 8 in a vertebral stabilizing system for fastening together at least two vertebrae V1 and V2 is described below with reference to FIG. 3.

Each vertebra V1, V2 has a respective median plane PV1, PV2 substantially perpendicular to the axis Ar of the spine of which it is a part and a respective posterior wall PPV1, PPV2 defining a posterior median plane PPr of said spine.

The stabilizing system includes at least two anchor members 26 and 28 respectively screwed into the posterior walls PPV1 and PPV2 of the vertebrae V1 and V2 so that a line L that intersects the two anchor members 26 and 28 is substantially parallel to said axis Ar of the spine. The two first or fixing portions 20' and 22' of a connecting member 8 interconnect the two anchor members 26 and 28 so that said median plane Pm defined by said branches 12 and 14 is substantially parallel to said posterior median plane PPr of said spine. In this way, the vertebrae V1 and V2, which are interconnected in their posterior portions, are relatively movable along the axis Ar of the spine.

Thus when the spine is stretched, the vertebrae V1 and V2 move away from each other in respective directions E and −E, which causes the threaded shanks 30 to move away from each other, deforming the connecting member 8, and in particular its flexible part 10. The deformed connecting member has its concave side facing away from the spine.

When the spine is bent, the inverse effect occurs and the vertebrae V1 and V2 move towards each other, which induces deformation of the connecting member with its concave side facing toward the spine.

Obviously, because it can bend more than prior art connecting rods, the connecting member 8 of the invention increases the mobility of the vertebrae relative to each other. Also, because of its construction, with two parallel branches 12, 14 connected together at their ends and extended by the rigid parts 20, 22, the connecting member 8 allows the spine to bend and extend in the plane Pa while at the same time limiting bending in the plane Pm perpendicular to the plane Pa. Thus the spine is stabilized laterally and relative movement of the vertebrae is limited.

In a particular embodiment, not shown, the connecting member has three rigid rod-forming parts interconnected by flexible parts. To this end, the central rigid part has two second portions extending respective ends of said fixing portion, said second portions respectively extending the ends of the two interconnected branches of the two flexible parts. The rigid parts extend the ends of the interconnected branches so that the median planes of both flexible parts are substantially the same. A longitudinal member is thus obtained having two rigid first portions, one at each end, and a central rigid part between the two rigid first portions, the rigid parts being interconnected in pairs by flexible parts.

The connecting member therefore maintains the spacing between the three anchor members that it interconnects, which members are fixed to three substantially equidistant vertebrae, to align them. Each rigid part of the connecting member is fixed to an anchor member so that there is a flexible part between pairs of vertebrae. In this way a single connecting member stabilizes three vertebrae, which reduces the time needed to assemble the stabilizing system as a whole and consequently the operating time. Also, because the three vertebrae are interconnected by a single connecting member, their mobility relative to one another is better controlled.

It goes without saying that providing connecting members having more than three rigid parts separated by flexible parts would not depart from the scope of the invention.

The invention claimed is:

1. A connecting member for maintaining the spacing between at least two anchor members screwed into vertebrae, the connecting member comprising:
   a flexible part comprising a first branch and a second branch defining a median plane, wherein the first branch and second branch are symmetrically spaced about a longitudinal axis of said connecting member, wherein a first end of the first branch and a first end of the second branch are interconnected to form a first end of the flexible part, and wherein a second end of the first branch and a second end of the second branch are interconnected to form a second end of the flexible part; and
   a first rigid rod forming part and a second rigid rod forming part, wherein the first rigid rod forming part extends from the first end of the flexible part and the second rigid rod forming part extends from the second end of the flexible part, wherein the first rigid rod forming part and second rigid rod forming part extend in opposite directions along the longitudinal axis and wherein the first rigid rod forming part and second rigid rod forming part each have a portion adapted to be secured in a rod receiving head portion of an anchor member;
   wherein said first and second branches of said flexible part have portions parallel to each other and to said longitudinal axis of said connecting member, a distance between said parallel portions being at least equal to a length of said parallel portions;
   wherein the cross-section of each of said first and second branches is less than the cross-section of each of said first and second rigid rod-forming parts so that said connecting member is able to bend elastically, on relative movement of the vertebrae, about an axis lying in the median plane that is perpendicular to the longitudinal axis when said connecting member is implanted in a human body with the first and second rigid rod-forming parts secured in the rod receiving head portions of corresponding anchor members; and
   wherein the connecting member is adapted to be implanted in the human body as a portion of a spinal stabilization system.

2. A connecting member according to claim 1, adapted to interconnect n anchor members, the connecting member being characterized in that it comprises n rigid rod-forming parts between which there are disposed n−1 flexible parts along the longitudinal axis of said member so that the median planes of all the flexible parts are substantially the same.

3. A connecting member according to claim 1, wherein each of said first and second rigid rod forming parts have a first cross-sectional area and the first and second branches have a total cross-sectional area that is less than the first cross-sectional area.

4. A connecting member according to claim 1, characterized in that the distance between the first end and second end of the first branch and the distance between the first end and second end of the second branch lies in the range 1.5 times to 2.5 times the distance between said parallel portions.

5. A connecting member according to claim 1, characterized in that the rigid rod-forming parts have a circular cross-section.

6. A connecting member according to claim 1, characterized in that it is made of titanium alloy.

7. A connecting member according to claim 1, characterized in that a sum of surface areas of sections of said first and second branches of said flexible part is less than a total of surface areas of said first and second rigid rod-forming parts.

8. A connecting member according to claim 1, wherein a diameter of said first branch is less than 70% of the diameter of said first rigid rod-forming part.

9. A connecting member according to claim 1, wherein a diameter of said first branch is in a range of 50% to 70% of the diameter of said first rigid rod-forming part.

10. A vertebral stabilization system for fastening together at least two vertebrae each having a median plane substantially perpendicular to the axis of the spine of which they are part and a posterior wall defining a posterior median plane of said spine, said system comprising:
   at least two anchor members each adapted to be fixed into the posterior wall of a vertebra so that a line which intersects said two anchor members is substantially parallel to said axis of the spine, each anchor member comprising a shank and a rod receiving head configured to secure a spinal stabilization rod;
   a connecting member connected between the at least two anchor members, the connecting member further comprising:
      a flexible part comprising a first branch and a second branch defining a median plane substantially parallel to said posterior median plane of the spine, wherein the first branch and second branch are symmetrically spaced about a longitudinal axis of said connecting member, wherein a first end of the first branch and a first end of the second branch are interconnected to form a first end of the flexible part, and wherein a second end of the first branch and a second end of the second branch are interconnected to form a second end of the flexible part; and
      a first rigid rod forming part and a second rigid rod forming part, wherein the first rigid rod forming part extends from the first end of the flexible part and the second rigid rod forming part extends from the second end of the flexible part, wherein the first rigid rod forming part and second rigid rod forming part extend in opposite directions along the longitudinal axis and wherein the first rigid rod forming part and second rigid rod forming part each have a portion adapted to be secured in a rod receiving head portion of an anchor member;
   wherein said first and second branches of said flexible part have portions parallel to each other and to said longitudinal axis of said connecting member, a distance between said parallel portions being at least equal to a length of said parallel portions;
   wherein the cross-section of each of said first and second branches is less than the cross-section of each of said first and second rigid rod-forming parts so that said connecting member is able to bend elastically about an axis that is perpendicular to the longitudinal axis, whereby said vertebrae, which are interconnected in their posterior portions, are relatively movable along said axis of said spine.

11. The system of claim 10, wherein each of said first and second rigid rod forming parts have a first cross sectional area and the first and second branches have a total cross-sectional area that is less than the first cross-sectional area.

12. The system according to claim 10, characterized in that the distance between the ends of said branches connected in pairs lies in the range 1.5 times to 2.5 times the distance between said branches.

13. The system according to claim 10, characterized in that the said rigid rod forming parts have a circular cross-section.

14. The system according to claim 10, wherein the connecting member is formed of titanium alloy.

15. The system according to claim 10, wherein the connecting member is adapted to interconnect n anchor members, the connecting member being characterized in that it comprises n rigid rod-forming parts between which there are disposed n−1 flexible parts along the longitudinal axis of said member so that the median planes of all the flexible parts are substantially the same.

16. The system according to claim 10, wherein a sum of surface areas of sections of said first and second branches of said flexible part is less than a total of surface areas of said first and second rigid rod-forming parts.

17. The system according to claim 10, wherein a diameter of said first branch is less than 70% of the diameter of said first rigid rod-forming part.

18. The system according to claim 10, wherein a diameter of said first branch is in a range of 50% to 70% of the diameter of said first rigid rod-forming part.

* * * * *